United States Patent [19]
Albelda et al.

[11] Patent Number: 5,496,172
[45] Date of Patent: Mar. 5, 1996

[54] PNEUMATIC REMOVER FOR USE IN REMOVING DENTAL PROSTHETICS

[76] Inventors: David Albelda, 5 Franklin Ave., White Plains, N.Y. 10601; Kafri Moshe, Beit Yeoshua, Beit Yeoshua, Israel, 40591; Christian Bat-Genstein, 1 Rue Poirier, Saint Mande, France, 94160

[21] Appl. No.: 292,808

[22] Filed: Aug. 10, 1994

[51] Int. Cl.$^6$ .............................. A61C 1/07; A61C 3/03; A61C 3/08
[52] U.S. Cl. ............................................ 433/120; 433/150
[58] Field of Search ..................... 433/150, 151, 433/120, 121, 118

[56] References Cited

U.S. PATENT DOCUMENTS

| | | | |
|---|---|---|---|
| 394,464 | 12/1888 | Custer | 433/120 |
| 419,381 | 1/1890 | Thomas et al. | 433/120 X |
| 443,691 | 12/1890 | West | 433/121 |
| 618,324 | 1/1899 | Blum | 433/120 X |
| 2,129,212 | 9/1938 | Hollenback | 433/120 X |
| 4,300,885 | 11/1981 | Khait | 433/151 |

FOREIGN PATENT DOCUMENTS

2204966  5/1974  France .............. A61C 3/16

*Primary Examiner*—Nicholas D. Lucchesi
*Attorney, Agent, or Firm*—Ohlandt, Greeley, Ruggiero & Perle

[57] ABSTRACT

A pneumatic remover assembly having a central housing with a reciprocating internal mass and spring, a first end unit having a spool-type valve for activating the remover, a second end unit having various conduits disposed therein for introducing and exhausting compressed air in and out of the remover, and a unique adjustment ring which is capable of adjusting the flow rate of the compressed air which is introduced to the remover, thereby regulating the striking intensity of the remover. The adjustment ring comprises an airflow groove disposed within the interior surface of the adjustment ring which is in contact with the second end unit of the remover assembly. This airflow groove has a gradually increasing depth along its length and is in continuous communication with the compressed air injection conduit disposed in the second end unit.

10 Claims, 6 Drawing Sheets

180
PNEUMATIC REMOVER FOR USE IN REMOVING DENTAL PROSTHETICS

The present invention generally relates to an adjustable pneumatic remover and in particular to a device used to remove fabricated crowns and bridges from teeth restored in such a manner.

BACKGROUND OF THE INVENTION

The fabricated dental prosthetic, usually formed from precious metals, porcelain, composite materials, or a combination, has proven to be a very functional and durable dental restoration, and is intended to be permanently affixed to the underlying tooth. On many occasions, however, it is necessary for the dentist to remove the dental prosthetic to provide further or more comprehensive treatment, to treat conditions that may arise, or for a variety of other medical reasons. More often than not, it is desirable to remove the crown or bridge in such a way that the underlying tooth and its supporting mechanism will remain intact, and will not be harmed or compromised in any way.

The removal of dental prosthetics, such as crowns, bridges and the like, has remained substantially a manual procedure wherein the dentist uses a forceps, hook, or pliers to extract the prosthetic from the tooth. Prosthetics which are affixed via a strong adhesive are extremely difficult to remove and often require painful and time consuming surgery to aid in the extraction.

The most widely accepted dental prosthetic remover is in the form of a pliers. However, pliers require the exertion of substantial force by the dentist which causes pain to the patient and often results in the damaging of the prosthetic device making it unusable for future restorations. Due to the high cost of replacing dental prosthetics, the effort exerted by the dentist and the pain inflicted upon the patient, it has been most desirable within the dental profession to develop a device which rapidly and painlessly removes prosthetics, while substantially lessening the number of prosthetics which are damaged during the removal process.

Recent advances in the development of pneumatic extractor devices has provided simple and quick extraction of dental prosthetics with minimal physical exertion by the dentist and pain to the patient. One such device is described in French Patent No. 2204966. The extractor, according to French Patent No. 2204966, utilizes compressed air which is introduced into a central portion of the extractor to actuate a hammer disposed about the central portion. This extractor is operated by a ball and pin control valve. A hook extractor appliance is affixed to the end of the extractor which is opposite to that end wherein compressed air is introduced into the central portion. The hook extractor appliance moves in the same direction of the hammer movement during the course of operation.

The extractor device according to French Patent No. 2204966 has a number of disadvantages. Firstly, the amount or flow of compressed air or strike intensity cannot be controlled via the device itself. That is, the air flow into the central portion of the extractor will be the same as the air flowing from the compressed air supply tank. It would be most desirable to be able to control the amount of compressed air that enters the extractor so as to provide for varied amounts of force (i.e., strike intensity) generated by the extractor during operation. Secondly, the use of a moving part such as a marble or ball in the air control valve can cause system failure due to misalignment or blockage of the air conduits. Finally, it would be desirable to have an extractor device which is capable of being connected directly to the multipurpose utility dental chair hoses which are readily available in most dental examining rooms. French Patent No. 2204966 requires the use of a separate and distinct compressed air hose which will require substantial installation costs associated with the use of this extractor design.

The present invention overcomes the inherent disadvantages of French Patent No. 2204966 by providing a remover device having a gentle, fingertip, push-button operation which is capable of providing the required striking intensity for crown or bridge removal. This steady strike action reduces slippage once the dental appliance is properly positioned about the prosthetic. Its minimal recoil action provides increased patient comfort, while sure and steady strikes reduce replacement costs. The present invention also provides a means for controlling the compressed air flow into the remover device which allows for preset, controlled uniformity of strike intensity which reduces damage to reusable crowns and bridges. The ability to control the air flowing into the remover also allows for its use in the removal of prosthetics with either temporary or permanent adhesives which necessitate different amounts of air flow or striking intensity to perform the function of removing the prosthesis from the tooth or gum. Moreover, the present invention is readily connected to virtually any conventional two, three or four hole dental chair utility hose (compressed air port, vacuum port, water port and light port). Thus, avoiding the high cost of retro-fitting each dental examining room with a separate compressed air line or hose.

The present invention also provides many additional advantages which shall become apparent as described below.

SUMMARY OF THE INVENTION

A pneumatic remover assembly which comprises: a housing unit which comprises an outer housing, a work chamber disposed within the outer housing, a shaft member centrally disposed within the work chamber, an internal mass reciprocally disposed about the shaft member, and a spring means disposed between the internal mass and a rear end of the housing unit, the shaft member having a first conduit means disposed along its entire length which allows for passage of a compressed air or gas therethrough; a first end unit disposed at an end of the housing unit such that the internal mass is disposed between the spring means and the first end unit, the first end unit comprising a valve mean, a means for securing a dental appliance to the first end unit, a second conduit means for introducing the compressed air or gas from the first conduit means to the valve means, a third conduit means disposed within the valve means which is capable of passing the compressed air or gas from the second conduit means through the valve means, and a fourth conduit means for removing the compressed air or gas from the valve means and introducing the compressed air or gas into the work chamber where it is capable of acting on the internal mass by moving it away from the first end unit; a second end unit disposed at the opposite end of the housing unit from the first end unit such that the spring means is disposed between the second end unit and the internal mass, the second end unit comprising a fifth conduit means which is capable of introducing the compressed air or gas into the first conduit means of the shaft member, at least one sixth conduit means capable of removing the compressed air or gas from the center chamber and out of the assembly; and a means for adjusting the flow rate of the compressed air or gas which is introduced to the pneumatic remover assembly via the fifth conduit means.

The means for adjusting the flow rate of the compressed air or gas is an adjustment ring and a seventh conduit means disposed between the adjustment ring and the fifth conduit means. The adjustment ring comprises an airflow groove disposed about the surface of the adjustment ring which is in contact with the second end unit, the airflow groove has a gradually increasing depth along its length and is in communication with the seventh conduit means.

A dental appliance for use in removing dental crowns and bridge from outside of the gum or palate which comprises an elongated stem portion and a means for gripping a dental prosthetic being disposed at about a 90° angle from the elongated stem portion.

A dental appliance for use in removing dental crowns and bridge from inside of the gum or palate which comprises an elongated stem portion, a second stem portion disposed at an angle of about 17 degrees 30 minutes from the elongated stem portion, a third stem portion disposed at an angle of about 38 degrees from the elongated stem portion, and a means for gripping a dental prosthetic disposed at an angle of about 90 degrees from the third stem portion.

A dental appliance for use in removing dental crowns and bridge located in the front of the mouth which comprises an elongated stem portion and a second stem portion disposed at an angle of about 16 degrees from the elongated stem portion.

Other and further objects, advantages and features of the present invention will be understood by reference to the following specification in conjunction with the annexed drawings, wherein like parts have been given like numbers.

BRIEF DESCRIPTION OF THE DRAWINGS

FIG. 5b is a cross-sectional view along line 5—5 of FIG. 5a;

DESCRIPTION OF THE PREFERRED EMBODIMENTS

A pneumatic remover assembly having a central housing with a reciprocating internal mass or hammer and spring, a first end unit having a spool-type valve for activating the remover, a second end unit having various conduits disposed therein for introducing and exhausting compressed air in and out of the remover, and a unique adjustment ring which is capable of adjusting the flow rate of the compressed air which is introduced to the remover and, thus, controlling the striking intensity of the remover. The adjustment ring comprises an airflow groove disposed about the surface of the adjustment ring which is in contact with the second end unit of the remover assembly. This airflow groove has a gradually increasing depth along its length and is in continuous communication with the compressed air injection conduit disposed in the second end unit.

Figure 1:
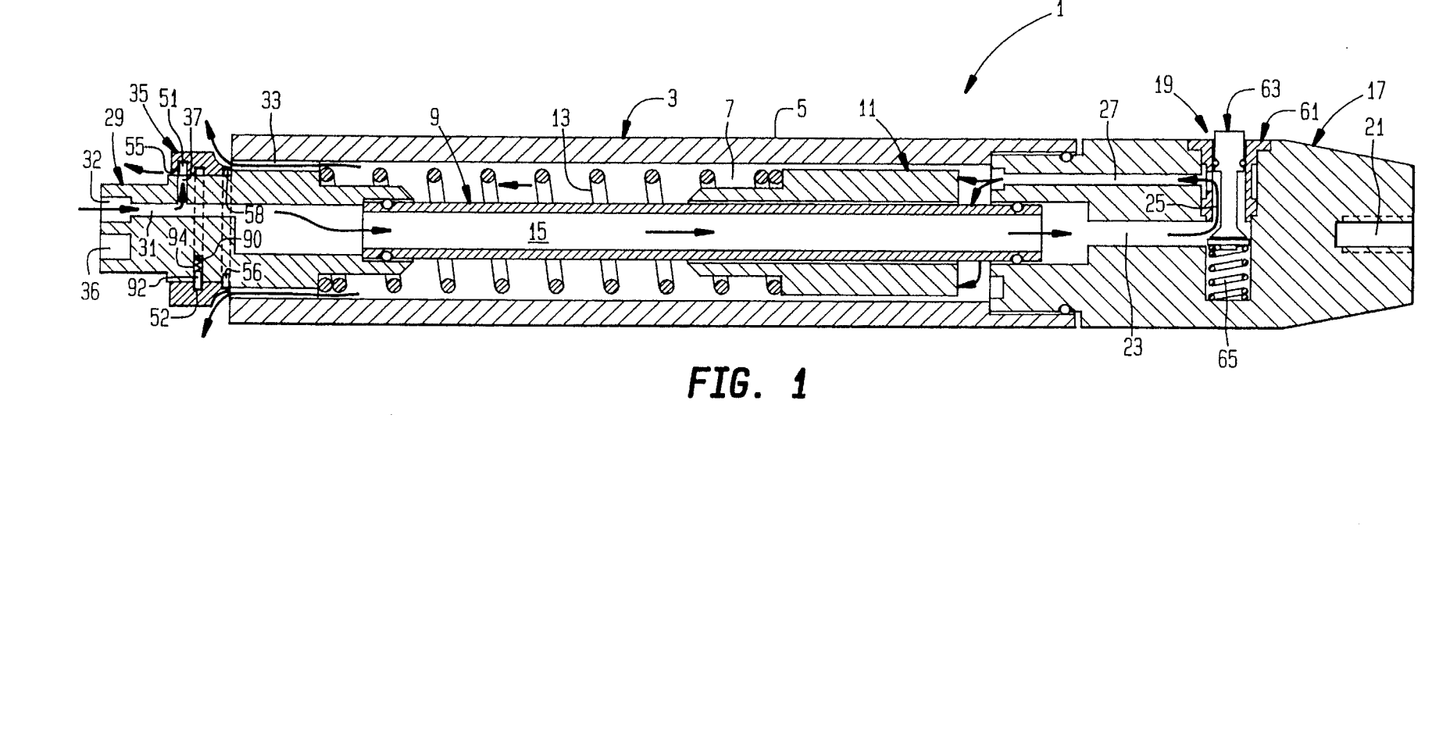
FIG. 1 is a schematic representation of a pneumatic remover according to the present invention.

The present invention can best be described by referring to the accompanying drawings wherein FIG. 1 is a schematic representation of the pneumatic remover assembly according to the present invention. FIG. 1 is in cross-section to permit clear description of the remover assembly 1.

Pneumatic remover assembly 1 has a housing unit 3 which comprises an outer housing 5, a work chamber 7 disposed within outer housing 5, shaft member 9 centrally disposed within work chamber 7, an internal mass 11 reciprocally disposed about shaft member 9, and a spring means 13 disposed between internal mass 11 and a rear end of housing unit 3. Shaft member 9 includes a first conduit means 15 centrally disposed along its entire length which allows for passage of a compressed air or gas therethrough.

Pneumatic remover assembly 1 also includes a first end unit 17 disposed at an end of housing unit 3 such that internal mass 11 is disposed between spring means 13 and first end unit 17. First end unit 17 comprising a valve means 19, a means for securing 21 a dental appliance to first end unit 17, a second conduit means 23 for introducing the compressed air or gas from first conduit means 15 to valve means 19, a third conduit means 25 disposed within valve means 19 which is capable of passing the compressed air or gas from second conduit means 23 through valve means 19, and a fourth conduit means 27 for removing the compressed air or gas from valve means 19 and introducing the compressed air or gas into work chamber 7 where it is capable of acting on internal mass 11 by moving it away from first end unit 17.

A second end unit 29 is disposed at the opposite end of housing unit 3 from first end unit 17 such that spring means 13 is disposed between second end unit 29 and internal mass 11. Second end unit 29 comprising a fifth conduit means 31 which is capable of introducing the compressed air or gas into first conduit means 15 of shaft member 9, at least one sixth conduit means 33 capable of removing the compressed air or gas from work chamber 7 and out of assembly 1.

Assembly 1 also include a means for adjusting the flow rate of the compressed air or gas which is introduced to pneumatic remover assembly 1 via fifth conduit means 31. Adjusting of the flow rate has a direct impact on the striking intensity applied to the respective dental prosthetic. The means for adjusting the flow rate of the compressed air or gas is an adjustment ring 35 and a seventh conduit means 37 disposed between adjustment ring 35 and fifth conduit means 31.

Figures 6, 7, 8:
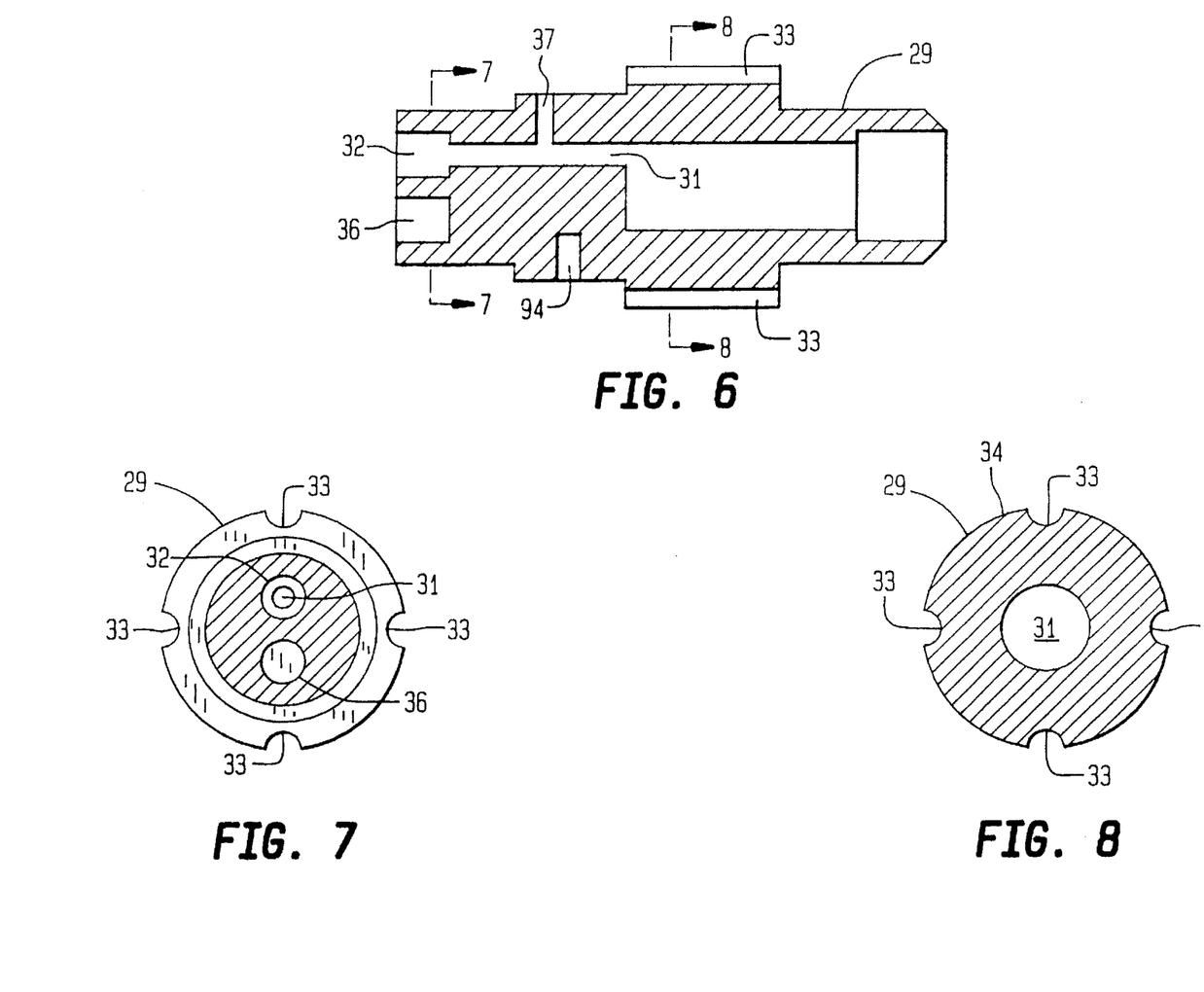
FIG. 6 is a schematic representation of the rear portion of the pneumatic remover of FIG. 1.
FIG. 7 is a cross-sectional view along line 7—7 of FIG. 6.
FIG. 8 is a cross-sectional view along line 8—8 of FIG. 6.
Figure 9:
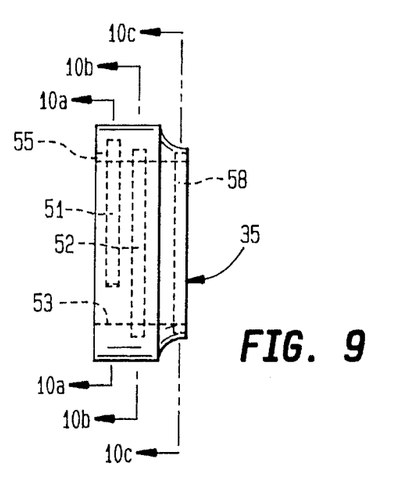
FIG. 9 is a side view of the pressure adjustment ring according to the present invention.
Figure 10A:
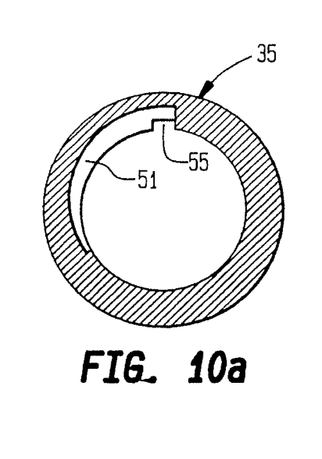
FIG. 10a is a cross-sectional view of the pressure adjustment ring along line 10a—10a of FIG. 9 showing the airflow groove.
Figure 10B:
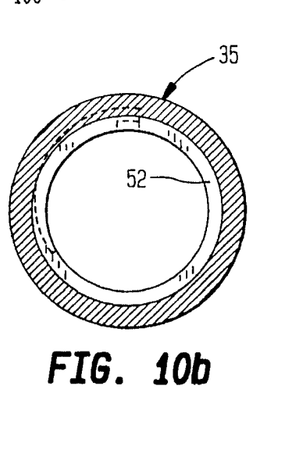
FIG. 10b is a cross-sectional view of the pressure adjustment ring along line 10b—10b of FIG. 9 showing the hole which houses the retaining pin.
Figure 10C:
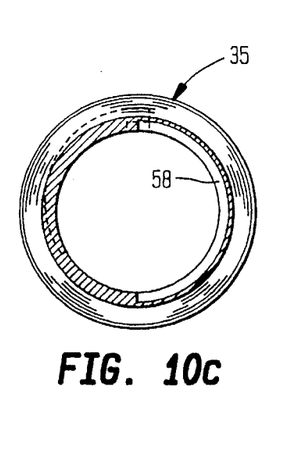
FIG. 10c is a cross-sectional view of the pressure adjustment ring along line 10c—10c of FIG. 9 showing the channel which restricts the rotational movement of the guide pin.

As shown in FIGS. 9, 10a, 10b and 10c, adjustment ring 35 comprises an airflow groove 51 disposed about interior surface 53 of adjustment ring 35 which is in contact with second end unit 29. Airflow groove 51 has a gradually increasing depth along its length and is in communication with seventh conduit means 37. Airflow groove 51 has an exhaust notch or exit port 55 which is disposed near rear surface 57 of adjustment ring 35 which permits the compressed air to exit from assembly 1. As shown in FIGS. 1 and 6, adjustment ring 35 is secured about second end unit 29 by means of a spring 90 and pin 92 disposed within seat 94 of second end unit 29 and hole 52 disposed in adjustment ring 35. The rotational movement of adjustment ring 35 is controlled by means of a guide pin 56 disposed between a channel 58 of adjustment ring 35 and second end unit 29. It is the length of channel 58 which restricts the rotational movement of adjustment ring 35.

Figure 2:
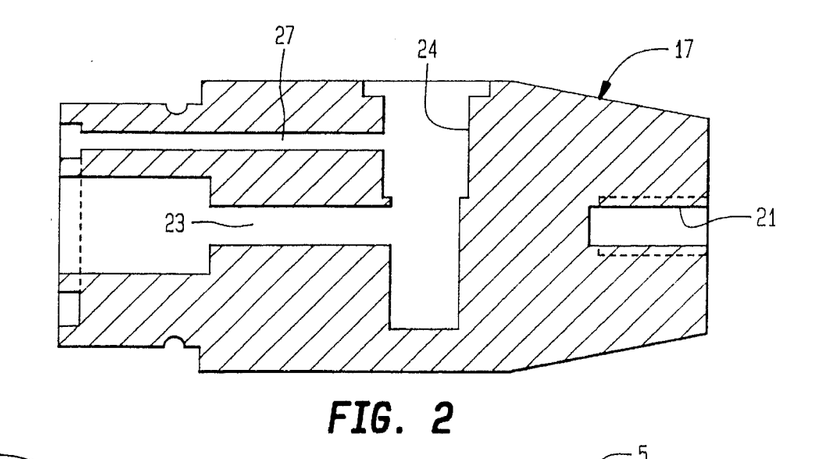
FIG. 2 is a schematic representation of the front portion of the pneumatic remover of FIG. 1.
Figure 3:
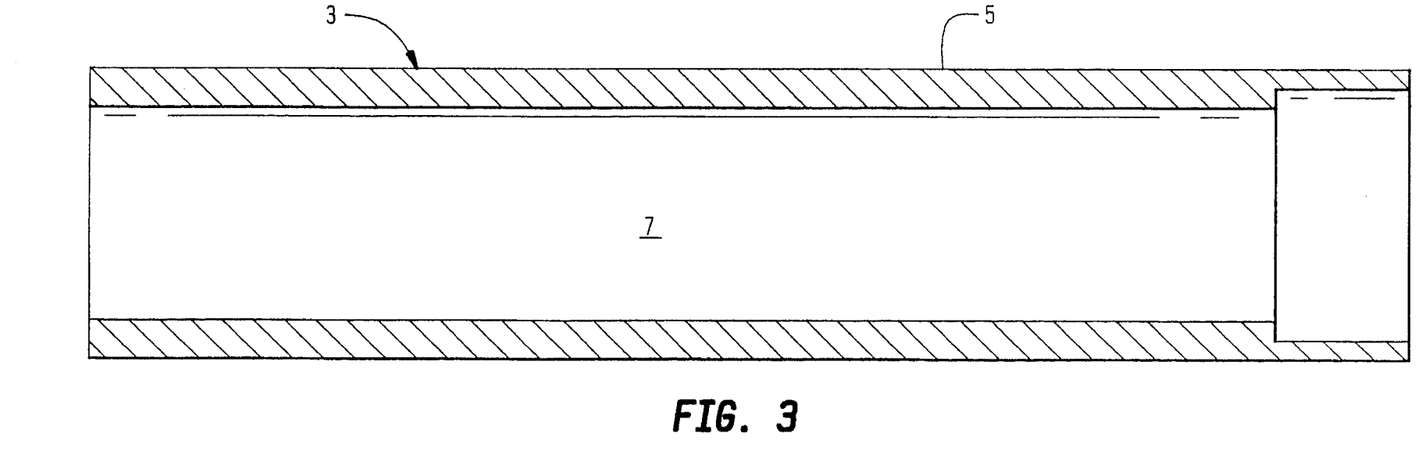
FIG. 3 is a schematic representation of the central housing of the pneumatic remover of FIG. 1.
Figure 4:
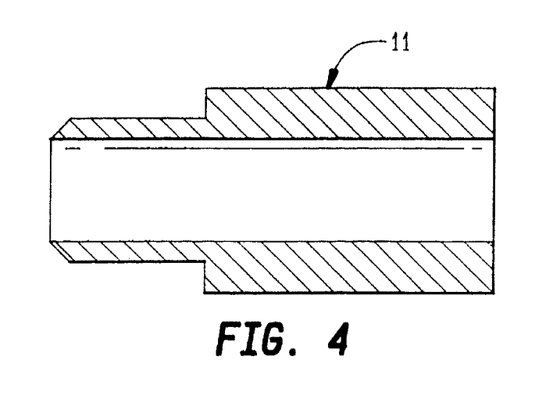
FIG. 4 is a schematic representation of the internal mass of the pneumatic remover of FIG. 1.
Figure 5A:
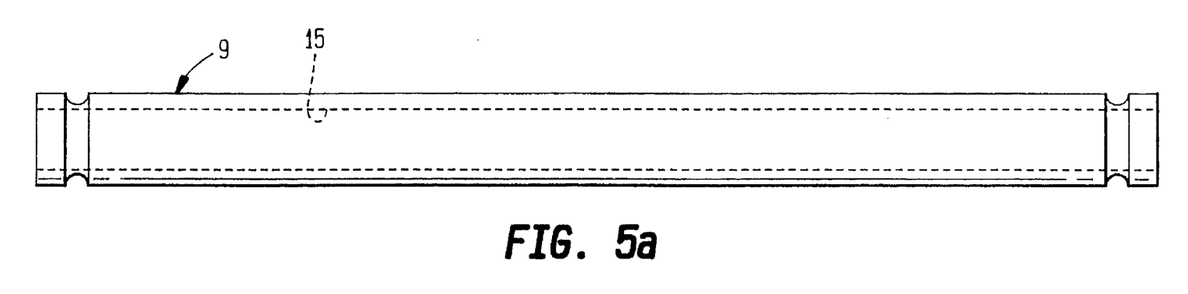
FIG. 5a is a schematic representation of the shaft means of the pneumatic remover of FIG. 1.
Figure 5B:
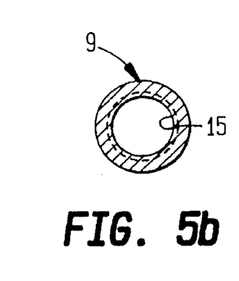
Figure 11:
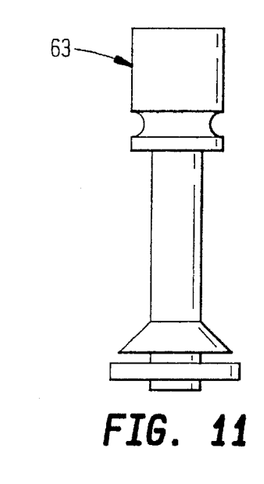
FIG. 11 is a schematic representation of the valve spool according to the present invention.
Figure 12:
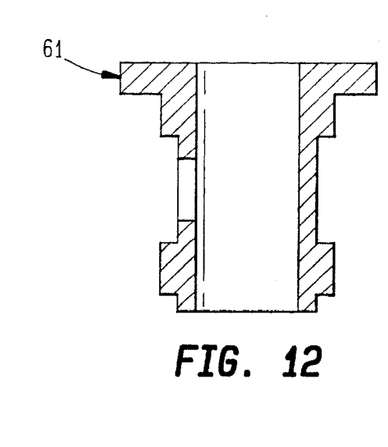
FIG. 12 is a schematic representation of the valve body according to the present invention.

As shown in FIGS. 1, 11 and 12 valve means 19 comprises a valve housing 61, a valve stem or spool 63, and a spring 65, whereby third conduit means 25 which is disposed within valve means 19 is in the open position when valve stem 63 is depressed and in the closed position when valve stem 63 is returned to its normal position. Spring 65 and valve housing 61 are initially disposed within valve seat 24 shown in FIG. 2, followed by the placement of valve stem 63 inside of valve housing 61.

Sixth conduit means 33 which is capable of removing the compressed air or gas from the center chamber is preferably a groove with a concave shape. Groove 33 is typically disposed along exterior surface 34 of second end unit 29 such that it is formed between exterior surface 34 and the interior surface of outer housing 5.

Figure 13:
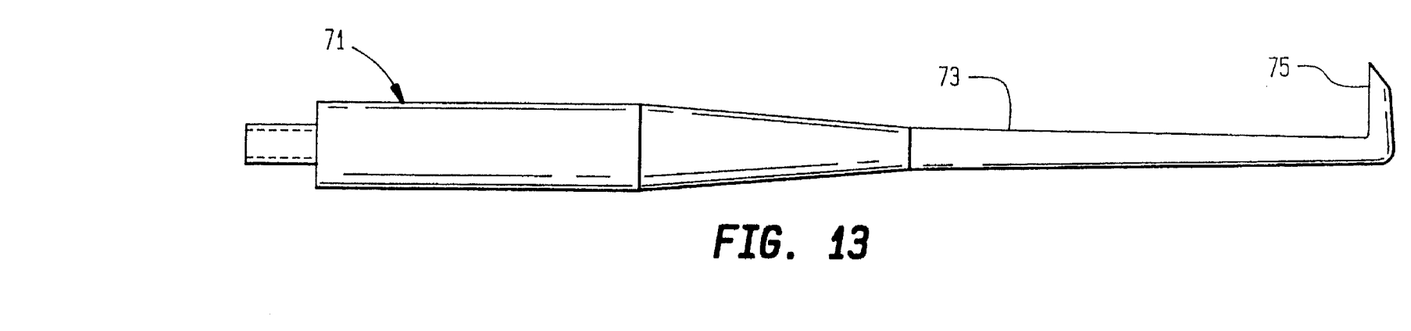
FIG. 13 is a dental appliance for use in removing dental crowns and bridge from outside of the gum or palate.
Figure 14:
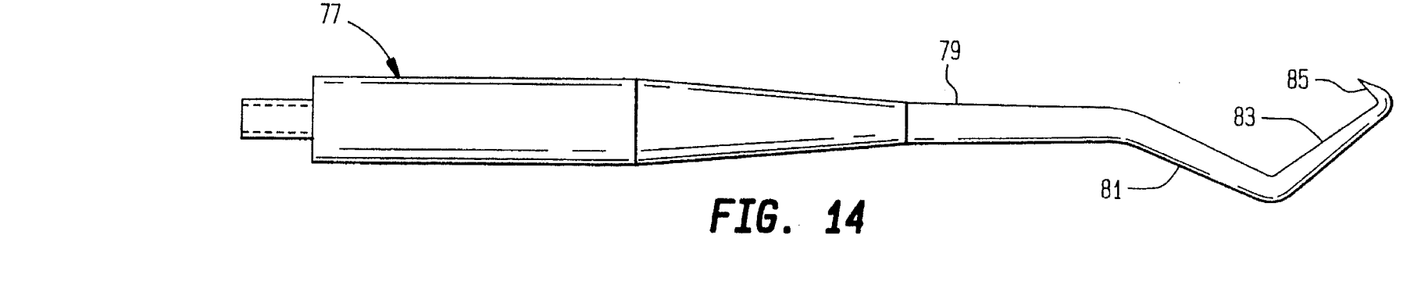
FIG. 14 is a dental appliance for use in removing dental crowns and bridge from inside of the gum or palate.
Figure 15:
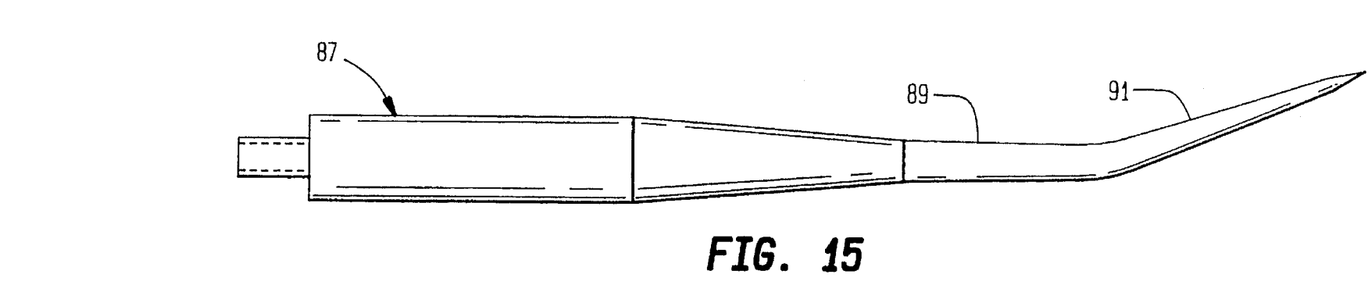
FIG. 15 is a dental appliance for use in removing dental crowns and bridge located in the front of the mouth.

FIGS. 13–15 depict various unique dental appliances which are useful with remover assembly 1 according to the present invention. Each dental appliance is replaceably affixed to first end unit 17 by threaded means 21 for securing the dental appliance thereto. The dental appliance preferably has a threaded portion at one end thereof which is screwed into threaded means 21 for securing it to first end unit 17 of remover assembly 1.

FIG. 13 depicts a dental appliance 71 for use in removing dental crowns and bridge from outside of the gum or palate. This dental appliance 71 comprises an elongated stem portion 73 and a means 75 for gripping a dental prosthetic being disposed at about a 90° angle from elongated stem portion 73.

FIG. 14 is a dental appliance 77 for use in removing dental crowns and bridge from inside of the gum or palate. This dental appliance 77 comprises an elongated stem portion 79, a second stem portion 81 disposed at an angle of about 17 degrees 30 minutes from elongated stem portion 79, a third stem portion 83 disposed at an angle of about 38 degrees from elongated stem portion 79, and a means 85 for gripping a dental prosthetic disposed at an angle of about 90 degrees from second stem portion 81.

FIG. 15 is a dental appliance 87 for use in removing dental crowns and bridge located in the front of the mouth. This dental appliance 87 comprises an elongated stem portion 89 and a second stem portion 91 disposed at an angle of about 16 degrees from elongated stem portion 89.

During use, pneumatic remover assembly 1 is connected to a conventional dental chair utility hose comprising 2, 3 or 4 basic dental utilities, i.e., compressed air, vacuum, water, or light. For demonstration purposes only, FIGS. 1 and 7 depict a remover assembly 1 which is suitable for connection with a two utility dental hose (i.e., water and compressed air). The compressed air male injection port (not shown) is inserted into female port 32 such that the compressed air is capable of unrestrictedly entering conduit 31 of second end unit 29. The water male injection port (not shown) is inserted into dead-end female port 36 such that the water is incapable of entering conduit 31 or any interior portion of remover assembly 1. One of dental appliances (71, 77, 87) is selected depending upon the intended application and secured to first end unit 17 by screwing into threaded means 21. The desired striking intensity and operating air pressure is determined using the conventional foot regulator. The basic strike intensity is controlled with foot pedal pressure, while finer modification is regulated by rotation of adjustment ring 35 about second end unit 29 wherein reduced striking intensity is obtained by allowing more compressed air to pass through conduit 37, airflow groove 51 and notch 55. That is, the larger the depth of airflow groove 51 at the intersection with conduit 37, the more compressed air can exit via conduit 37. Increased striking intensity is therefore obtained by reducing the amount of compressed air which exits assembly 1 via conduit 37. In that instance, it would be desirable to have less depth in airflow groove 51 at the intersection with conduit 37. Conversely, if less striking intensity is desired, then a greater depth in airflow groove 51 at the intersection with conduit 37 would be required.

For removal of a crown, the dental appliance (71, 77, 87) is positioned at the least sensitive point of the crown margin. The strike is delivered by depressing valve stem 63 such that compressed air from the dental chair utility hose enters conduit 31, a predetermined amount compressed air is diverted via conduit 37 and removed from assembly 1 via adjustment ring 35 to establish the desired striking intensity, and passes through conduit 15 of shaft means 9 where it enters conduit 23. When valve stem 63 is depressed conduit 25 is opened such that compressed air passes therethrough into conduit 27. The compressed air is carried along conduit 27 into work chamber 7 where it causes internal mass or hammer 11 to move toward second end unit 29, while spring 13 is compressed. It is the movement of internal mass or hammer 11 which provides the force required to remove the dental prosthetic in the same direction without any substantial physical exertion by the dentist. After the strike is delivered valve 63 returns to its normal position by releasing valve stem 63, thereby closing conduit 25 which prevents any additional compressed air from entering work chamber 7. Any residual compressed air left in work chamber 7 from the previous strike is exhausted from remover assembly via conduit 33. Conduit 33 is preferably a plurality of grooves disposed about the exterior surface 34 of second end unit 29.

It is preferable that all pans of extract assembly 1 be fabricated from either aluminum or stainless steel in order to permit sterilization thereof so as to avoid the transmission of infectious disease from patient to patient.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A pneumatic remover assembly which comprises:

a housing unit which comprises an outer housing, a work chamber disposed within said outer housing, a shaft member centrally disposed within said work chamber, an internal mass reciprocally disposed about said shaft member, and a spring means disposed between said internal mass and a rear end of said housing unit, said shaft member having a first conduit means disposed along its entire length which allows for passage of a compressed air or gas therethrough;

a first end unit disposed at an end of said housing unit such that said internal mass is disposed between said spring means and said first end unit, said first end unit comprising a valve means, a means for securing a dental appliance to said first end unit, a second conduit means for introducing said compressed air or gas from said first conduit means to said valve means, a third conduit means disposed within said valve means which is capable of passing said compressed air or gas from said second conduit means through said valve means, and a fourth conduit means for removing said compressed air or gas from said valve means and introducing said compressed air or gas into said work chamber where it is capable of acting on said internal mass by moving it away from said first end unit;

a second end unit disposed at the opposite end of said housing unit from said first end unit such that said spring means is disposed between said second end unit and said internal mass, said second end unit comprising a fifth conduit means which is capable of introducing said compressed air or gas into said first conduit means of said shaft member, at least one sixth conduit means capable of removing said compressed air or gas from said center chamber and out of said assembly; and a means for adjusting the flow rate of said compressed air or gas which is introduced to said pneumatic remover assembly via said fifth conduit means.

2. The pneumatic remover assembly according to claim 1 wherein said means for adjusting the flow rate of said compressed air or gas is an adjustment ring disposed about said second end unit and a seventh conduit means disposed between said adjustment ring and said fifth conduit means.

3. The pneumatic remover assembly according to claim 2 wherein said adjustment ring comprises an airflow groove disposed about the interior surface of said adjustment ring which is in contact with said second end unit, said airflow groove has a gradually increasing depth along its length and is in communication with said seventh conduit means.

4. The pneumatic remover assembly according to claim 3 further comprising a exit port connected to one end of said airflow groove and disposed at an outer surface of said adjustment ring, whereby compressed air which passes through said airflow groove can exit said adjustment ring via said exit port.

5. The pneumatic remover assembly according to claim 3 wherein said adjustment ring is movably disposed about said second end unit by means of a guide pin disposed within said second end unit and a channel of predetermined length disposed within an interior surface of said adjustment ring; whereby said adjustment ring can be rotated about said guide pin in order to control the depth of said airflow groove which is disposed opposite said seventh conduit means.

6. The pneumatic remover assembly according to claim 1 wherein said valve means comprises a valve housing, a valve stem and a valve spring, whereby said third conduit means which is disposed within said valve means is in the open position when said valve stem is depressed such that said spring is in a compressed state and in the closed position when said valve stem is returned to its normal position and said spring is in an expanded state.

7. The pneumatic remover assembly according to claim 1 wherein said sixth conduit means which is capable of removing said compressed air or gas from said center chamber is a groove disposed between said second end unit and said outer housing, said groove being formed on the exterior surface of said second end unit.

8. The pneumatic remover assembly according to claim 1 further comprising a dental appliance affixed to said first end unit by said means for securing said dental appliance thereto, said dental appliance comprising an elongated stem portion and a means for gripping a dental prosthetic being disposed at about a 90° angle from said elongated stem portion.

9. The pneumatic remover assembly according to claim 1 further comprising a dental appliance affixed to said first end unit by said means for securing said dental appliance thereto, said dental appliance comprising an elongated stem portion, a second stem portion disposed at an angle of about 17 degrees 30 minutes from said elongated stem portion, a third stem portion disposed at an angle of about 38 degrees from said elongated stem portion, and a means for gripping a dental prosthetic disposed at an angle of about 90 degrees from said second stem portion.

10. The pneumatic remover assembly according to claim 1 further comprising a dental appliance affixed to said first end unit by said means for securing said dental appliance thereto, said dental appliance comprising an elongated stem portion, and a second stem portion disposed at an angle of about 16 degrees from said elongated stem portion.

* * * * *